United States Patent
Pazenok et al.

(10) Patent No.: US 8,916,710 B2
(45) Date of Patent: Dec. 23, 2014

(54) METHOD FOR PRODUCING TETRAZOLE-SUBSTITUTED ANTHRANILIC ACID DIAMIDE DERIVATIVES BY REACTING PYRAZOLIC ACIDS WITH ANTHRANILIC ACID ESTERS

(75) Inventors: Sergii Pazenok, Solingen (DE); Frank Volz, Köln (DE); Norbert Lui, Odenthal (DE); Arnd Neeff, Burscheid (DE); Sylvia Szywalski, Leverkusen (DE)

(73) Assignee: Bayer Intellectual Property GmbH, Monheim am Rhein (DE)

( * ) Notice: Subject to any disclaimer, the term of this patent is extended or adjusted under 35 U.S.C. 154(b) by 0 days.

(21) Appl. No.: 14/131,147

(22) PCT Filed: Jul. 5, 2012

(86) PCT No.: PCT/EP2012/063169
§ 371 (c)(1),
(2), (4) Date: Feb. 10, 2014

(87) PCT Pub. No.: WO2013/007604
PCT Pub. Date: Jan. 17, 2013

(65) Prior Publication Data
US 2014/0235865 A1  Aug. 21, 2014

Related U.S. Application Data
(60) Provisional application No. 61/506,265, filed on Jul. 11, 2011.

(30) Foreign Application Priority Data
Jul. 8, 2011  (EP) ..................................... 11173325

(51) Int. Cl.
C07D 401/14 (2006.01)
C07D 403/06 (2006.01)

(52) U.S. Cl.
CPC .................................. C07D 401/14 (2013.01)
USPC ....................................... 546/268.4; 548/253

(58) Field of Classification Search
USPC ....................................... 546/268.4; 548/253
See application file for complete search history.

(56) References Cited

U.S. PATENT DOCUMENTS

| | | |
|---|---|---|
| 8,324,390 B2 | 12/2012 | Fischer et al. |
| 8,410,106 B2 | 4/2013 | Fischer et al. |
| 2010/0029478 A1 | 2/2010 | Alig et al. |
| 2010/0256195 A1 | 10/2010 | Fischer et al. |
| 2011/0257191 A1 | 10/2011 | Fischer et al. |

FOREIGN PATENT DOCUMENTS

| | | |
|---|---|---|
| WO | 2004020445 A2 | 3/2004 |
| WO | 2007144100 A1 | 12/2007 |
| WO | 2008070158 A1 | 6/2008 |
| WO | 2010069205 A2 | 6/2010 |
| WO | 2010069502 | 6/2010 |
| WO | 2011098408 | 8/2011 |
| WO | 2011098408 A2 | 8/2011 |

OTHER PUBLICATIONS

International Search Report corresponding to PCT/EP2012/063169 mailed Aug. 14, 2012.
Norris, William P., "5-Trifluoromethylterazole and Its Derivatives", Organic Chemistry Branch, Chemistry Division, U.S. Naval Ordnance Test Station, vol. 27, pp. 3248-3251, Mar. 19, 1962.
Brown et al., "5-Perfluoroalkyletazoles. I. Ring-Opening Reactions", Department of Chemistry and Department of Chemical Engineering, University of Florida, pp. 1871-1873, Jun. 1967.
Curran et al., "tris (2-Perfluorohexylehyl)tin azide: A New Reagent for Preparation of 5-Substituted Tetrazoles from Nitriles with Purification by Fluorous/Organic Liquid-Liquid Extraction", Tetrahedron, (1999), vol. 55, pp. 8997-9006.
Hansen et al., "Thermodynamics of Proton Ionization from Some Substituted, Unsaturated, Five-Membered Nitrogen Heterocycles (I)", Department of Chemistry, University of New Mexico, vol. 7. pp. 991-996, Aug. 1970.
International Search Report for PCT/EP2012/063169 Mailed Aug. 22, 2012.

*Primary Examiner* — Patricia L Morris
(74) *Attorney, Agent, or Firm* — Miles and Stockbridge

(57) ABSTRACT

The present invention relates to a process for preparing tetrazole-substituted anthranilic acid diamide derivatives of the formula (I)

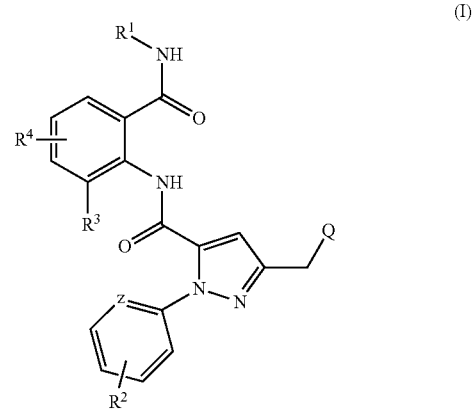

in which $R^1$, $R^2$, $R^3$, $R^4$, Q and Z have the meanings given in the description, by reacting pyrazole acids with anthranilic esters.

8 Claims, No Drawings

METHOD FOR PRODUCING TETRAZOLE-SUBSTITUTED ANTHRANILIC ACID DIAMIDE DERIVATIVES BY REACTING PYRAZOLIC ACIDS WITH ANTHRANILIC ACID ESTERS

CROSS REFERENCE TO RELATED APPLICATIONS

This application is a §371 National Stage Application of PCT/EP2012/063169, filed Jul. 5, 2012, which claims priority to European Application No. 11173325.9, filed Jul. 8, 2011, and claims benefit of U.S. Provisional Application No. 61/506,265, filed Jul. 11, 2011.

BACKGROUND OF THE INVENTION

1. Field of the Invention

The present invention relates to a process for preparing tetrazole-substituted anthranilic acid diamide derivatives of the formula (I)

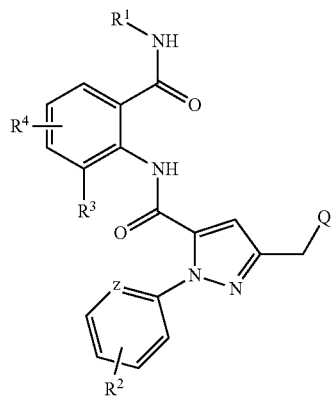

by reacting N-aryl- and N-hetaryl-substituted pyrazole acids containing methylenetetrazole radicals with anthranilic esters and amines.

2. Description of Related Art

It has already been described in the literature that tetrazole-substituted anthranilic acid diamide derivatives can be prepared by reacting tetrazole-substituted N-aryl- and N-hetaryl-substituted pyrazole acids with anthranilamides (cf. WO2010/069502). It is also possible to obtain tetrazole-substituted anthranilic acid diamide derivatives by reacting tetrazole-substituted benzoxazinones with amines (WO 2010/069502). Both processes afford a good, but in some cases only moderate, yield; in particular, the proportion of regioisomers where the tetrazole ring Q is attached in two different positions may vary. Accordingly, it is an object of the present invention to provide novel economical processes for preparing tetrazole-substituted anthranilic acid diamide derivatives of the formula (I) in higher purity and high quality which, in particular, afford a constant ratio of the two possible regioisomers.

SUMMARY

The object was achieved in accordance with the present invention by a process for preparing anthranilic acid diamide derivatives of the general formula (I)

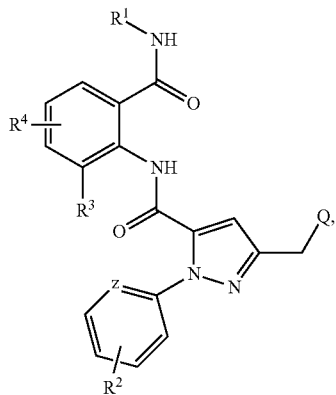

in which $R^1$, $R^3$ independently of one another represent hydrogen, or represent $C_1$-$C_6$-alkyl, $C_1$-$C_6$-alkoxy, $C_2$-$C_6$-alkenyl, $C_2$-$C_6$-alkynyl or $C_3$-$C_6$-cycloalkyl which are each optionally mono- or polysubstituted by identical or different halogen or nitro substituents, preferably represent ($C_1$-$C_5$)-alkyl, particularly preferably represent methyl, ethyl or tert-butyl, very particularly preferably represent methyl, $R^2$ represents $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro, alkylamino, dialkylamino, cycloalkylamino or $C_3$-$C_6$-trialkylsilyl, preferably represents halogen or $C_1$-$C_6$-alkyl, particularly preferably represents fluorine or chlorine, very particularly represents chlorine, $R^4$ represents hydrogen, halogen, cyano, nitro $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, $SF_5$, $C_1$-$C_4$-alkylthio, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_4$-alkoxy)imino, ($C_1$-$C_4$-alkyl)(C-$C_4$-alkoxy)imino, ($C_1$-$C_4$-haloalkyl)(C-$C_4$-cyano, nitro, alkoxy)imino or $C_3$-$C_6$-trialkylsilyl, preferably represents hydrogen, chlorine or cyano, particularly preferably represents chlorine or cyano, very particularly preferably represents cyano, Q represents a tetrazole ring which is monosubstituted by $R^5$, preferably represents a tetrazole ring which is monosubstituted by $R^5$ and selected from the group consisting of

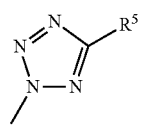

Q-1

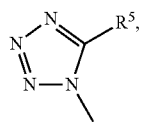

Q-2 particularly preferably represents Q-1, also particularly preferably represents Q-2, $R^5$ represents $C_1$-$C_5$-alkyl which may be mono- to trisubstituted by halogen, preferably represents $C_1$-$C_3$-perfluoroalkyl, particularly preferably represents $CF_3$ or $C_2F_5$, very particularly preferably represents $CF_3$, Z represents CH or N, preferably represents N, the compounds of the general formula (I) furthermore include N-oxides and salts, characterized in that tetrazole-substituted pyrazole acids of the formula (II)

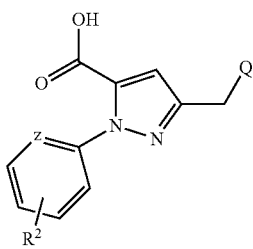
(II)

in which $R^2$, Q and Z have the meanings given above, are reacted with anthranilic acid esters of the formula (III)

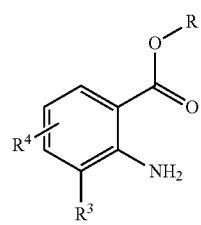
(III)

in which

R represents alkyl, cycloalkyl, alkoxyalkyl, arylalkyl, thioalkyl, alkylthioalkyl, alkylsulphonylalkyl, cyanoalkyl, haloalkyl, nitroalkyl or aryl, preferably represents methyl, ethyl, ($C_5$-$C_{12}$)-alkyl or aryl, particularly preferably represents methyl, ethyl, pentyl, hexyl or 2-ethylhexyl, $R^3$, $R^4$ have the meanings given above, to give compounds of the formula (IV)

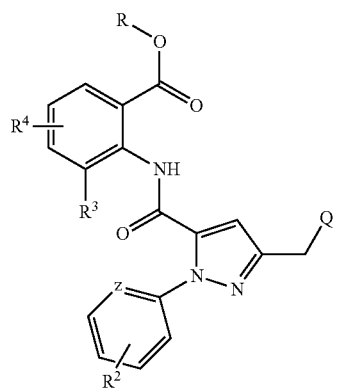
(IV)

in which R, $R^2$, $R^3$, $R^4$, Q and Z have the meanings given above, and these compounds of the general formula (IV) are reacted with amines of the general formula (V)

$R^1NH_2$ (V)

in which $R^1$ has the meanings given above, to give anthranilamides of the formula (I),

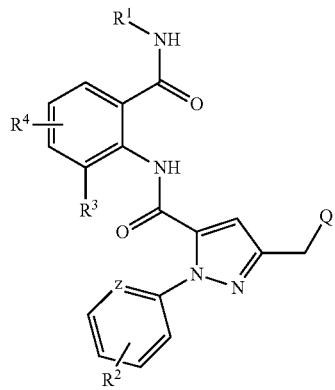
(I)

in which $R^1$, $R^2$, $R^3$, $R^4$, Q and Z have the meanings given above.

DETAILED DESCRIPTION OF A PREFERRED EMBODIMENT

The process according to the invention provides the compounds of the formula (1) in a purity of >90%, preferably 91%-97%, particularly preferably 95% to 97%, where the isomer ratio of the two possible regioisomers remains constant at from 90:10 to 96:4 (main isomer A, where Q represents Q-1: minor isomer B, where Q represents Q-2).

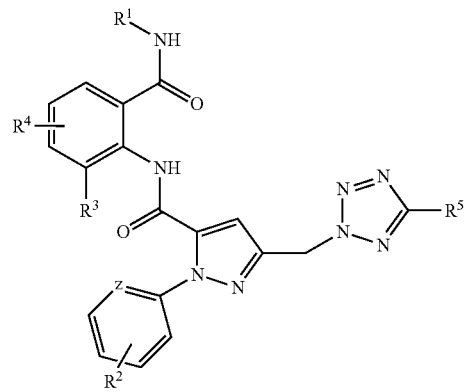
(A)

Main isomer A

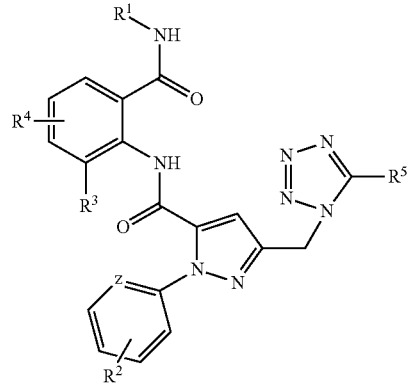
(B)

Minor isomer B

The process according to the invention can be illustrated by Scheme (I) below:

Scheme (I)

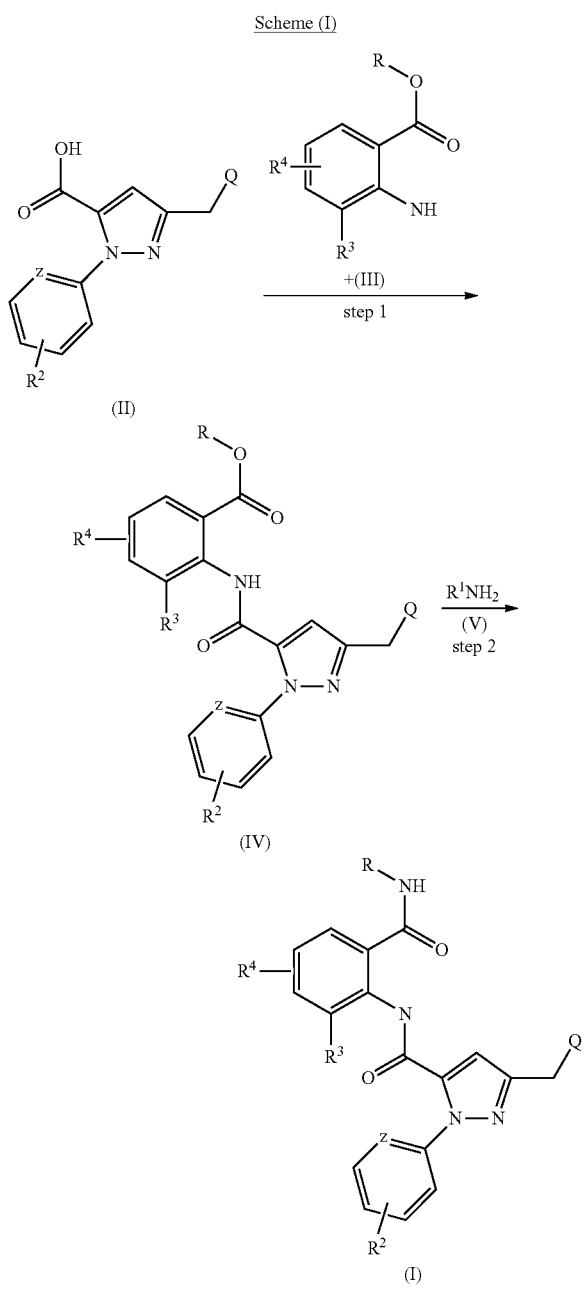

in which R, $R^1$, $R^2$, $R^3$, $R^4$, Q and Z have the general meanings indicated above.

General Definitions:

In the context of the present invention, the term halogens (X) comprises, unless defined otherwise, elements selected from the group consisting of fluorine, chlorine, bromine and iodine, with fluorine, chlorine and bromine being preferred and fluorine and chlorine being particularly preferred. Substituted groups may be mono- or polysubstituted, where in the case of polysubstitution the substituents can be identical or different.

Alkyl groups substituted by one or more halogen atoms (-X) (=haloalkyl groups) are, for example, selected from trifluoromethyl ($CF_3$), difluoromethyl ($CHF_2$), $CCl_3$, $CFCl_2$, $CF_3CH_2$, $ClCH_2$, $CF_3CCl_2$.

In the context of the present invention, alkyl groups are, unless defined otherwise, straight-chain or branched hydrocarbon groups. In the context of the present invention, alkyl groups can be mono- or polysubstituted by further groups; for example, cyanoalkyl groups are selected from cyanomethyl, cyanoethyl, etc., nitroalkyl groups are selected, for example, from nitromethyl, nitroethyl, etc.

Alkoxyalkyl groups are alkyl groups substituted by alkoxy; specifically this comprises, for example, the meanings methoxymethyl, ethoxymethyl, propoxyethyl, etc.

The definitions alkyl and $C_1$-$C_{12}$-alkyl include, for example, the meanings methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

In the context of the present invention, cycloalkyl groups are, unless defined otherwise, cyclic saturated hydrocarbon groups.

In the context of the present invention, aryl radicals are, unless defined otherwise, aromatic hydrocarbon radicals which may have one, two or more heteroatoms selected from O, N, P and S and may optionally be substituted by further groups.

In the context of the present invention, arylalkyl groups and arylalkoxy groups are, unless defined otherwise, alkyl and alkoxy groups, respectively, which are substituted by aryl groups and may have an alkylene chain. Specifically, the definition arylalkyl includes, for example, the meanings benzyl- and phenylethyl; the definition arylalkoxy includes, for example, the meaning benzyloxy.

In the context of the present invention, alkylaryl groups (alkaryl groups) and alkylaryloxy groups are, unless defined otherwise, aryl groups and aryloxy groups, respectively, which are substituted by alkyl groups and may have a $C_{1-8}$-alkylene chain and may have one or more heteroatoms selected from O, N, P and S in the aryl skeleton or aryloxy skeleton.

If appropriate, the compounds according to the invention may be present as mixtures of various possible isomeric forms, in particular of stereoisomers, such as, for example, E and Z, threo and erythro, and also optical isomers, and, if appropriate, also of tautomers. What are disclosed are both the E and the Z isomers, and also the threo and erythro, and the optical isomers, any mixtures of these isomers and the possible tautomeric forms.

Step 1.

The compounds of the formula (IV) are obtained by reacting tetrazole-substituted pyrazole acids of the formula (II) with anthranilic esters of the formula (III).

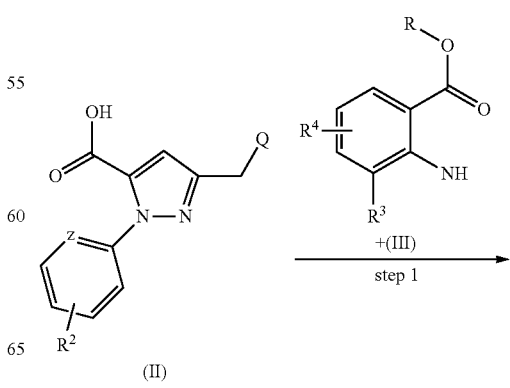

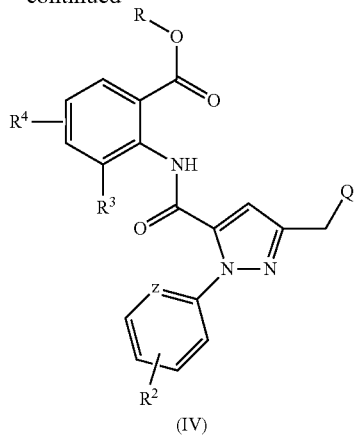

(IV)

Anthranilic esters of the formula (III) are known (cf. WO 2008/070158). Pyrazole acids of the formula (II) are likewise known (cf. WO2007/144100). Pyrazole acids of the formula (II) can be prepared, for example, from halomethylpyrazole esters of the formula (VI) and perfluoroalkyltetrazoles of the formula (VII) in two steps a and b (cf. Scheme (II) and Preparation Examples). Here, the compounds of the formula (VIII) formed are converted by basic hydrolysis (step b) into the pyrazole acids of the formula (II).

Scheme (II)

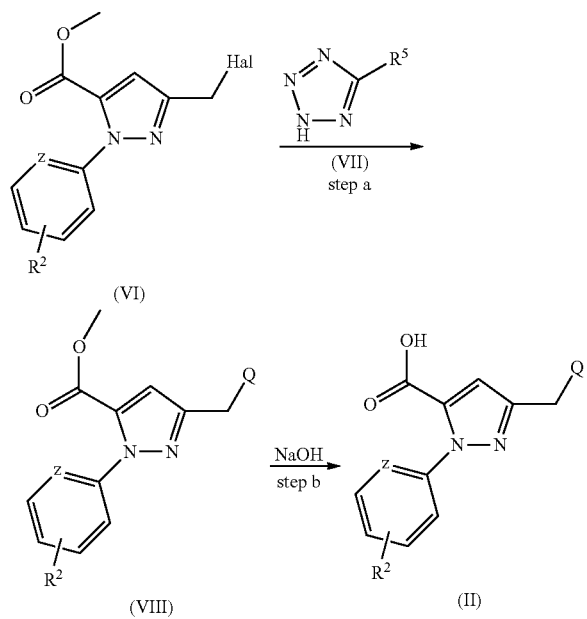

Halomethylpyrazole esters of the formula (VI) are likewise known and can be prepared as described in WO 2011/7073101. Perfluoroalkyltetrazoles of the formula (VII) are known; some of them are even commercially available, or they can be obtained by known processes (cf., for example, WO2004/020445; William P. Norris, *J. Org. Chem.*, 1962, 27 (9), 3248-3251; Henry C. Brown, Robert J. Kassal, *J. Org. Chem.*, 1967, 32 (6), 1871-1873; Dennis P Curran, Sabine Hadida, Sun-Young Kim, *Tetrahedron*, 1999, 55 (29), 8997-9006; L. D. Hansen, E. J. Baca, P. Scheiner, *Journal of Heterocyclic Chemistry*, 1970, 7, 991-996, JACS V.27, p. 3248).

Step 1

As a basic principle, Step 1 is carried out in the presence of a base. Suitable bases are, for example, sodium hydroxide, potassium carbonate, sodium carbonate, caesium carbonate, sodium methoxide. Preference is given to organic bases such as trialkylamines, pyridines, alkylpyridines, phosphazenes and 1,8-diazabicyclo[5.4.0]undecene (DBU). Particular preference is given to pyridines, alkylpyridines such as β-picoline, 2,6-dimethylpyridine, 2-methyl-5-ethylpyridine, 2,3-dimethylpyridine. When carrying out Process Step 1 according to the invention, preferably from 1.5 mol to 4 mol, particularly preferably from 1.5 to 3 equivalents, of the base are employed per mole of the pyrazole of the formula (II). Step 1 is carried out in the presence of a condensing agent. Suitable for this purpose are all agents customary for such coupling reactions. Examples which may be mentioned are acid halide formers such as phosgene, phosphorus tribromide, phosphorus trichloride, phosphorus pentachloride, phosphorus oxychloride or thionyl chloride; anhydride formers such as ethyl chloroformate, methyl chloroformate, isopropyl chloroformate, isobutyl chloroformate or methanesulphonyl chloride, p-toluenesulphonyl chloride; carbodiimides such as N,N'-dicyclohexylcarbodiimide (DCC) or other customary condensing agents such as phosphorus pentoxide, polyphosphoric acid, 1,1'-carbonyldiimidazole, 2-ethoxy-N-ethoxycarbonyl-1,2-dihydroquinoline (EEDQ), triphenylphosphine/carbon tetrachloride, bromotripyrrolidinophosphonium hexafluorophosphate, bis(2-oxo-3-oxazolidinyl)phosphinic chloride or benzotriazol-1-yloxy-tris(dimethylamino)phosphonium hexafluorophosphate. Polymer-supported reagents such as, for example, polymer-bound cyclohexylcarbodiimide may also be used. Particularly suitable are methanesulphonyl chloride (mesyl chloride) and phosgene. When carrying out Process Step 1 according to the according to the invention, preferably from 1 mol to 3 mol, particularly preferably from 1.5 to 2.5 mol, of the condensing agent are employed per mole of the pyrazole of the formula (II).

The process step according to the invention is preferably carried out within a temperature range of from 0° C. to +80° C., particularly preferably at temperatures of from 10° C. to +50° C.

When carrying out the process step according to the invention, an equimolar amount of the compound of the formula (III) is employed per mole of the pyrazole acid of the formula (II).

The Process Step (1) according to the invention is generally carried out under atmospheric pressure. However, it is alternatively also possible to operate under reduced pressure or under elevated pressure.

The reaction time is not critical and may be chosen in a range between one and a plurality of hours, depending on the batch size, on the substituent $R^5$ and on the temperature.

Suitable solvents are, for example, aliphatic, alicyclic or aromatic hydrocarbons such as, for example, petroleum ether, n-hexane, n-heptane, cyclohexane, methylcyclohexane, benzene, toluene, xylene or decalin, and halogenated hydrocarbons such as, for example, chlorobenzene, dichlorobenzene, dichloromethane, chloroform, carbon tetrachloride, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoric triamide; sulphoxides such as dimethyl sulphoxide or sulphones such as sulpholane, alcohols such as methanol, ethanol, isopropanol, or solvent mixtures. Particular preference is given to using acetone, acetonitrile, toluene, methyl tert-butyl ether, THF. Particularly suitable are acetonitrile, THF, DMF and NMP.

Step 2

The compounds of the formula (IV) formed in Step 1 are converted into anthranilic acid diamide derivatives of the formula (I):

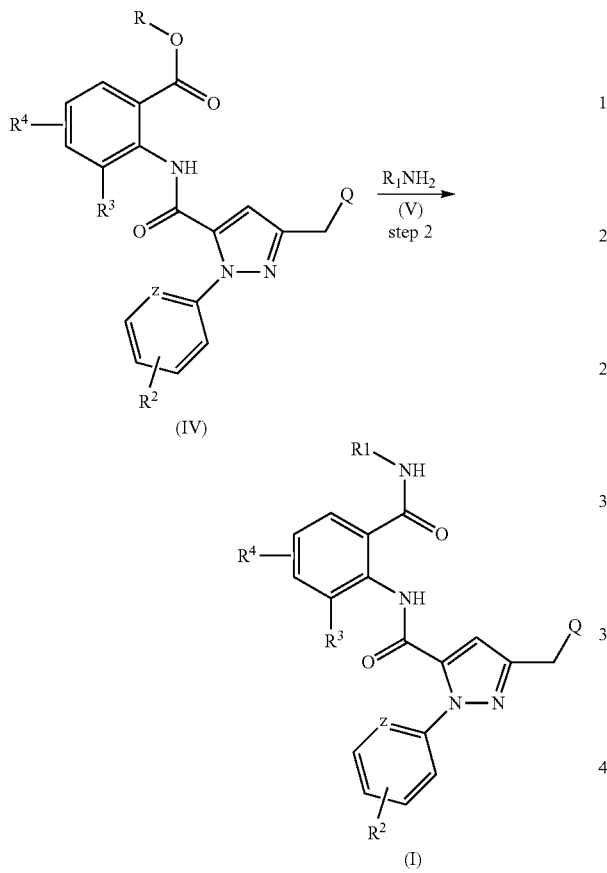

Surprisingly, it has now been found that the compounds of the formula (IV) react selectively and under very mild conditions to give anthranilic acid diamide derivatives of the formula (I). Very mild conditions are to be understood, for example, as meaning the following conditions; however, this is not limiting:

The reaction is generally carried out under atmospheric pressure. However, it is alternatively also possible to operate under elevated pressure (for example reaction with $MeNH_2$ in an autoclave).

Depending on the batch size and temperature, the reaction time can be chosen in a range between 1 hour and a plurality of hours.

The reaction step is preferably carried out in a solvent. Suitable solvents are, for example, selected from the group consisting of water, alcohols such as methanol, ethanol, isopropanol or butanol, aliphatic and aromatic hydrocarbons such as, for example, n-hexane, benzene or toluene which may be substituted by fluorine and chlorine atoms, such as methylene chloride, dichloroethane, chlorobenzene or dichlorobenzene; ethers such as, for example, diethyl ether, diphenyl ether, methyl tert-butyl ether, isopropyl ethyl ether, dioxane, diglyme, dimethyl glycol, dimethoxyethane (DME) or THF; nitriles such as methyl nitrile, acetonitrile, butyl nitrile or phenyl nitrile; amides such as dimethylformamide (DMF) or N-methylpyrrolidone (NMP), or mixtures of such solvents, with water, acetonitrile, dichloromethane and alcohols (ethanol) being particularly suitable. Particular preference is given to THF, acetonitrile, alcohols.

What are used are the compounds of the formula (V) where $R^1$ preferably represents $(C_1-C_6)$-alkyl.

The exchange may additionally be accelerated by addition of bases or acids. Suitable bases are alkali metal hydroxides such as, for example, lithium hydroxide, sodium hydroxide or potassium hydroxide, alkali metal carbonates such as, for example, $Na_2CO_3$, $K_2CO_3$, and acetates such as, for example, NaOAc, KOAc, LiOAc and alkali metal alkoxides such as, for example, NaOMe, NaOEt, NaOt-Bu, KOt-Bu, and organic bases such as trialkylamines, alkylpyridines, phosphazenes and 1,8-diazabicyclo[5.4.0]undecene (DBU). Preference is given to organic bases such as pyridines, alkylpyridines.

Suitable acids are $CH_3COOH$, $CF_3COOH$, p-TSA, HCl, $H_2SO_4$.

The Process Step (2) according to the invention is preferably carried out within a temperature range of from 0° C. to +100° C., particularly preferably at temperatures of from 10° C. to +80° C., very particularly preferably at 10-60° C.

The Process Step (2) according to the invention is generally carried out under atmospheric pressure. However, it is alternatively also possible to operate under reduced pressure or under elevated pressure in an autoclave.

Depending on the batch size and the temperature, the reaction time can be chosen in a range between 1 hour and a plurality of hours.

PREPARATION EXAMPLES

The following Preparation Examples illustrate the invention without limiting it.

Example 1

Isomer mixture of methyl 1-(3-chloropyridin-2-yl)-3-{[5-(trifluoromethyl)-2H-tetrazol-2-yl]methyl}-1H-pyrazole-5-carboxylate (main isomer) and methyl 1-(3-chloropyridin-2-yl)-3-{[5-(trifluoromethyl)-1H-tetrazol-1-yl]methyl}-1H-pyrazole-5-carboxylate (minor component). 2.86 g (0.01 mol) of methyl 3-(chloromethyl)-1-(3-chloropyridin-2-yl)-1H-pyrazole-5-carboxylate and 1.6 g (0.01 mol) of sodium 5-(trifluoromethyl)tetrazol-2-ide and 0.15 g of KI in 50 ml of acetone were heated at 56° C. for 9 hours. The salts were filtered off and the acetone was removed under reduced pressure. This gave 4.59 g of the product as a 9:1 mixture of the two isomers.

Analytical Characterization

Main Isomer $^1$H NMR ($CD_3CN$) δ: 8.52 (1H, d); 7.95 (1H, d), 7.45 (1H, dd); 7.10 (1H, s); 6.05 (2H, s); 3.75 (3H, s) ppm.

$^{19}$F NMR -64.05 ppm.

Minor Component $^{19}$F NMR -61.46 ppm.

$^1$H NMR ($CD_3CN$) δ: 8.50 (1H, d); 7.90 (1H, d), 7.45 (1H, dd); 6.95 (1H, s); 5.80 (2H, s); 3.70 (3H, s) ppm.

Example 2

Isomer mixture of 1-(3-chloropyridin-2-yl)-3-{[5-(trifluoromethyl)-2H-tetrazol-2-yl]methyl}-1H-pyrazole-5-carboxylic acid (main isomer) and 1-(3-chloropyridin-2-yl)-3-

[5-(trifluoromethyl)-1H-tetrazol-1-yl]-1H-pyrazole-5-carboxylic acid (minor component)

4.59 g of the mixture from Example 1 were dissolved in 40 ml of methanol, and 2 g of NaOH were added as a 10% strength solution in water. The mixture was stirred at RT for 3 hours.

The reaction mixture was heated to 50° C. and stirred at 50° C. for a total of 12 h. 30 ml of water were added, and the mixture was cooled to 10° C. The precipitate was filtered off and washed with water. This gave 4.63 g (85%) of the product as a mixture of the two regioisomers in a ratio of 93:7.

Analytical Characterization:

| H/C | δH/ppm | Mult. | rel. No. H | δH/ppm Isomer | Mult. | rel. No. H |
| --- | --- | --- | --- | --- | --- | --- |
| 1 | 8.00 | D | 1 | 8.00 | D | 1 |
| 2 | 8.01 | D | 1 | 8.01 | D | 1 |
| 3 | 3.70 | S | 3 | 3.70 | S | 3 |
| 4 | 10.58 | S | 1 | 10.57 | S | 1 |
| 5 | 2.26 | S | 3 | 2.25 | S | 3 |
| 6 | 7.42 | S | 1 | 7.36 | S | 1 |
| 7 | 6.34 | S | 2 | 6.12 | S | 2 |
| 8 | 8.49 | DD | 1 | 8.48 | DD | 1 |
| 9 | 7.61 | DD | 1 | 7.60 | DD | 1 |
| 10 | 8.18 | DD | 1 | 8.15 | DD | 1 |

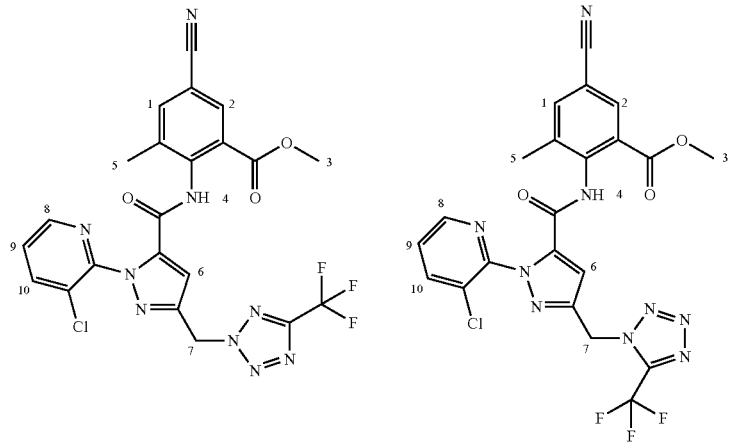

10% strength HCl was added to adjust the pH of the solution to 3, and the product was extracted with methyl tert-butyl ether. After removal of the solvent, the residue (4 g) is reacted further without purification.

Analytical Characterization Main Isomer 92%

$^1$H NMR (CD$_3$CN) δ: 13.5 (bs), 8.52 (1H, d); 8.2 (1H, d), 7.6 (1H, dd); 7.2 (1H, s); 6.25 (2H, s) ppm.

$^{19}$F NMR -64.25 ppm.

Example 3

Isomer mixture of methyl 2-({[1-(3-chloropyridin-2-yl)-3-{[5-(trifluoromethyl)-2H-tetrazol-2-yl]methyl}-1H-pyrazol-5-yl]carbonyl}amino)-5-cyano-3-methylbenzoate and methyl 2-({[1-(3-chloropyridin-2-yl)-3-{[5-(trifluoromethyl)-1H-tetrazol-1-yl]methyl}-1H-pyrazol-5-yl]carbonyl}amino)-5-cyano-3-methylbenzoate 3.73 g (10 mmol) of the mixture of 1-(3-chloropyridin-2-yl)-3-{[5-(trifluoromethyl)-2H-tetrazol-2-yl]methyl}-1H-pyrazole-5-carboxylic acid and 1-(3-chloropyridin-2-yl)-3-[5-(trifluoromethyl)-1H-tetrazol-1-yl]-1H-pyrazole-5-carboxylic acid in a ratio of 9:1 were initially charged in 20 ml of acetonitrile and cooled to 0° C., and first 1.97 g (27 mmol) of pyridine and then 1.93 g (17 mmol) of methanesulphonyl chloride were added at this temperature. The mixture was stirred at 0° C. for 1 hour, and 1.9 g (10 mmol) of methyl 2-amino-5-cyano-3-methylbenzoate and 0.79 g (10 mmol) of pyridine were then added at 0° C.

Example 4

Isomer mixture of ethyl 2-({[1-(3-chloropyridin-2-yl)-3-{[5-(trifluoromethyl)-2H-tetrazol-2-yl]methyl}-1H-pyrazol-5-yl]carbonyl}amino)-5-cyano-3-methylbenzoate and ethyl 2-({[1-(3-chloropyridin-2-yl)-3-{[5-(trifluoromethyl)-1H-tetrazol-1-yl]methyl}-1H-pyrazol-5-yl]carbonyl}amino)-5-cyano-3-methylbenzoate The procedure of Example 1 was followed; however, ethyl 2-amino-5-cyano-3-methylbenzoate was used.

Yield 81%.

Example 5

Isomer mixture of 1-(3-chloropyridin-2-yl)-N-[4-cyano-2-methyl-6-(methylcarbamoyl)-phenyl]-3-{[5-(trifluoromethyl)-2H-tetrazol-2-yl]methyl}-1H-pyrazole-5-carboxamide (main isomer) and 1-(3-chloropyridin-2-yl)-N-[4-cyano-2-methyl-6-(methylcarbamoyl)phenyl]-3-[5-(trifluoromethyl)-1H-tetrazol-1-yl]-1H-pyrazole-5-carboxamide (minor component) in a ratio of 93:7.

5.45 g of the isomer mixture of methyl 2-({[1-(3-chloropyridin-2-yl)-3-{[5-(trifluoromethyl)-2H-tetrazol-2-yl]methyl}-1H-pyrazol-5-yl]carbonyl}amino)-5-cyano-3-methylbenzoate and methyl 2-({[1-(3-chloropyridin-2-yl)-3-{[5-(trifluoromethyl)-1H-tetrazol-1-yl]methyl}-1H-pyrazol-5-yl]carbonyl}amino)-5-cyano-3-methylbenzoate were dissolved in 30 ml of acetonitrile. 1 equivalent of methylamine (as a solution in THF) was then added. The mixture was stirred at 30° C. for 4 hours and diluted with 30 ml of water, and the precipitate was filtered off. This gave 5.1 g (93%) of the product as a white solid having an isomer ratio of 93:7.

Analytical Characterization

Main Isomer 94%

| H/C | δH/ppm | Mult. | rel. No. H | δC/ppm | Mult. | rel. No. C |
|---|---|---|---|---|---|---|
| 1 | — | — | — | 118.7 | Q | 1 |
| 2 | — | — | — | 156.1 | Q | 1 |
| 3 | 6.34 | S | 2 | 51.3 | T | 1 |
| 4 | — | — | — | 145.6 | S | 1 |
| 5 | 7.40 | S | 1 | 108.5 | D | 1 |
| 6 | — | — | — | 138.8 | S | 1 |
| 7 | — | — | — | 156.3 | S | 1 |
| 8 | 10.55 | S | 1 | — | — | — |
| 9 | — | — | — | 137.6 | S | 1 |
| 10 | — | — | — | 138.7 | S | 1 |
| 11 | — | — | — | 166.2 | S | 1 |
| 12 | 8.38 | Q | 1 | — | — | — |
| 13 | 2.66 | D | 3 | 26.3 | Q | 1 |
| 14 | 7.75 | D | 1 | 129.7 | D | 1 |
| 15 | — | — | — | 109.4 | S | 1 |
| 16 | — | — | — | 118.3 | S | 1 |
| 17 | 7.87 | D | 1 | 135.2 | D | 1 |
| 18 | — | — | — | 138.0 | S | 1 |
| 19 | 2.20 | S | 3 | 18.0 | Q | 1 |
| 20 | — | — | — | 149.1 | S | 1 |
| 21 | — | — | — | 128.0 | S | 1 |
| 22 | 8.16 | DD | 1 | 139.4 | D | 1 |
| 23 | 7.60 | DD | 1 | 126.7 | D | 1 |
| 24 | 8.48 | DD | 1 | 147.3 | D | 1 |

Minor Component

| H/C | δH/ppm | Mult. | rel. No. H | δC/ppm | Mult. | rel. No. C |
|---|---|---|---|---|---|---|
| 1 | — | — | — | 118.1 | Q | 1 |
| 2 | — | — | — | 145.9 | Q | 1 |
| 3 | 6.11 | S | 2 | 47.0 | T | 1 |
| 4 | — | — | — | 145.9 | S | 1 |
| 5 | 7.35 | S | 1 | 107.7 | D | 1 |
| 6 | — | — | — | 138.8 | S | 1 |
| 7 | — | — | — | 156.2 | S | 1 |
| 8 | 10.54 | S | 1 | — | — | — |
| 9 | — | — | — | 137.6 | S | 1 |
| 10 | — | — | — | 135.2 | S | 1 |
| 11 | — | — | — | 166.2 | S | 1 |
| 12 | 8.37 | Q | 1 | — | — | — |
| 13 | 2.66 | D | 3 | 26.3 | Q | 1 |
| 14 | 7.75 | D | 1 | 129.7 | D | 1 |
| 15 | — | — | — | 109.3 | S | 1 |
| 16 | — | — | — | 118.3 | S | 1 |
| 17 | 7.87 | D | 1 | 135.4 | D | 1 |
| 18 | — | — | — | 138.0 | S | 1 |
| 19 | 2.19 | S | 3 | 17.9 | Q | 1 |
| 20 | — | — | — | 149.1 | S | 1 |
| 21 | — | — | — | 128.1 | S | 1 |
| 22 | 8.14 | DD | 1 | 139.4 | D | 1 |
| 23 | 7.58 | DD | 1 | 126.7 | D | 1 |
| 24 | 8.47 | DD | 1 | 147.2 | D | 1 |

Example 6

Isomer mixture of 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (main isomer) and 1-(3-chloropyridin-2-yl)-N-[4-cyano-2-methyl-6-(methylcarbamoyl)phenyl]-3-[5-(trifluoromethyl)-1H-tetrazol-1-yl]-1H-pyrazole-5-carboxamide (minor component) in a ratio of 93:7.

The procedure of Example 3 was followed; however, the isomer mixture of ethyl 2-({[1-(3-chloropyridin-2-yl)-3-{[5-(trifluoromethyl)-2H-tetrazol-2-yl]methyl}-1H-pyrazol-5-yl]carbonyl}amino)-5-cyano-3-methylbenzoate and ethyl 2-({[1-(3-chloropyridin-2-yl)-3-{[5-(trifluoromethyl)-1H-tetrazol-1-yl]methyl}-1H-pyrazol-5-yl]carbonyl}amino)-5-cyano-3-methylbenzoate was used.

The invention claimed is:

1. A process for preparing a compound of formula (I)

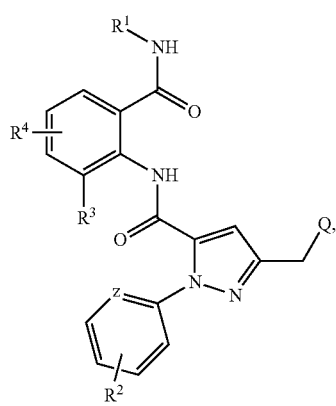

(I)

in which $R^1$, $R^3$ independently of one another represent hydrogen, or represent $C_1$-$C_6$-alkyl, $C_1$-$C_6$-alkoxy, $C_2$-$C_6$-alkenyl, $C_2$-$C_6$-alkynyl or $C_3$-$C_6$-cycloalkyl which are each optionally mono- or polysubstituted by identical or different halogen or nitro substituents, $R^2$ represents $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro, alkylamino, dialkylamino, cycloalkylamino or $C_3$-$C_6$-trialkylsilyl, $R^4$ represents hydrogen, halogen, cyano, nitro, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, $SF_5$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_4$-alkoxy)imino, ($C_1$-$C_4$-alkyl)($C_1$-$C_4$-alkoxy)imino, ($C_1$-$C_4$-haloalkyl)($C_1$-$C_4$-cyano, nitro, alkoxy)imino or $C_3$-$C_6$-trialkylsilyl, Q represents a tetrazole ring which is monosubstituted by $R^5$, $R^5$ represents $C_1$-$C_5$-alkyl which may be mono- to trisubstituted by halogen, Z represents CH or N, Wherein the compound of formula (I) furthermore may also comprise an N-oxide and/or a salt, comprising reacting a tetrazole-substituted pyrazole acid of formula (II)

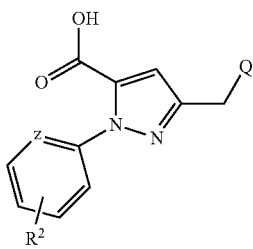

with an anthranilic ester of formula (III)

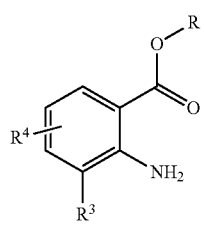

in which
R represents alkyl, cycloalkyl, alkoxyalkyl, arylalkyl, thioalkyl, alkylthioalkyl, alkylsulphonylalkyl, cyanoalkyl, haloalkyl, nitroalkyl or aryl,
to give a compound of formula (IV)

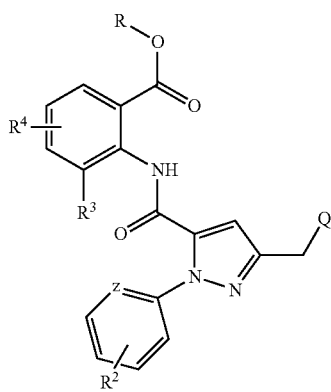

and reacting said compound of formula (IV) with an amine of general formula (V)

to give an anthranilamide of formula (I).

2. The process for preparing a compound according to claim 1, wherein
$R^1$, $R^3$ independently of one another represent $(C_1$-$C_5)$-alkyl,
$R^2$ represents halogen or $C_1$-$C_6$-alkyl,
$R^4$ represents hydrogen, chlorine or cyano,
Q represents a tetrazole ring which is monosubstituted by $R^5$ and selected from the group consisting of

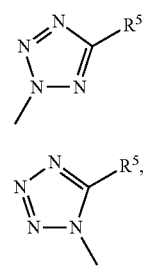

$R^5$ represents $(C_1$-$C_3)$-perfluoroalkyl,
Z represents N.

3. The process for preparing a compound according to claim 1, wherein
$R^1$, $R^3$ independently of one another represent methyl, ethyl or tert-butyl,
$R^2$ represents fluorine or chlorine,
$R^4$ represents chlorine or cyano,
Q represents Q-1 or Q-2,
$R^5$ represents $CF_3$ or $C_2F_5$,
Z represents N.

4. The process for preparing a compound according to claim 1, wherein $R^5$ represents $CF_3$.

5. The process for preparing a compound according to claim 1, wherein $R^2$ represents chlorine, $R^3$ represents methyl and $R^4$ represents cyano.

6. The process for preparing a compound according to claim 1, wherein a ratio of compound of formula (I) in which Q represents Q-1 to compound of formula (I) in which Q represents Q-2 is from 90:10 to 96:4.

7. The process for preparing a compound according to claim 1, wherein reaction of a pyrazole acid of formula (II) with an anthranilic ester of formula (III) is carried out with addition of a base.

8. The process for preparing a compound according to claim 1, wherein a compound of formula (IV) is reacted at a reaction temperature of from 0° C. to +100° C. with a compound of formula (V) to give an anthranilic acid diamide derivative of formula (I).

* * * * *